United States Patent [19]

Curtis et al.

[11] Patent Number: 4,990,681

[45] Date of Patent: Feb. 5, 1991

[54] METHOD FOR REMOVING HYDROGEN FLUORIDE FROM MIXTURES COMPRISING AROMATIC KETONES

[76] Inventors: Thomas A. Curtis, 100 Pinewood Rd. #310, Virginia Beach, Va. 23451; Timothy R. Ryan, 4914 Overbrook Cir., Corpus Christi, Tex. 78413; Daniel D. Lindley, 23 Am Vogelsang, D6239 Eppstein 3, Fed. Rep. of Germany

[21] Appl. No.: 445,055

[22] Filed: Dec. 4, 1989

[51] Int. Cl.$^5$ ............................................. C07C 45/80
[52] U.S. Cl. ..................................... 568/324; 568/319
[58] Field of Search ........................ 568/324, 410, 411

[56] References Cited

U.S. PATENT DOCUMENTS

| | | | |
|---|---|---|---|
| 3,403,183 | 9/1968 | Dobratz et al. | 568/324 |
| 4,059,633 | 10/1977 | Childs | 568/411 |
| 4,524,217 | 6/1985 | Davenport et al. | 564/223 |
| 4,568,763 | 2/1986 | Davenport et al. | 560/142 |
| 4,593,125 | 6/1986 | Davenport et al. | 568/319 |
| 4,607,125 | 8/1986 | Mott | 568/319 |
| 4,663,485 | 5/1987 | Murphy et al. | 568/324 |
| 4,692,546 | 9/1987 | Davenport | 568/319 |

FOREIGN PATENT DOCUMENTS

60-188343  9/1985  Japan* ........................... 568/543 F

*Primary Examiner*—James H. Reamer

*Attorney, Agent, or Firm*—Donald R. Cassady; Marvin Turken

[57] ABSTRACT

A method is provided for separating hydrogen fluoride (HF) from a mixture comprising HF complexed with an aromatic ketone in which the keto carbon atom is directly bonded to an aromatic ring carbon atom, e.g., 4-isobutylacetophenone, by adding a carboxylic acid anhydride, e.g., acetic anhydride, to the mixture while maintaining the mixture at conditions sufficient to sustain a reaction between the anhydride and the HF to form the corresponding acyl fluoride, e.g., acetyl fluoride, and carboxylic acid, e.g., acetic acid, and separating the acyl fluoride from the mixture. The method is conveniently carried out in a stripping column near the top of which the mixture comprising aromatic ketone and HF is fed and below which the anhydride is fed. Between these feed points, the uncomplexed HF is stripped from the mixture, while below the anhydride feed point or points, the anhydride reacts with the complexed HF to form the acyl fluoride which is stripped from the mixture, and the carboxylic acid. The separation method may be integrated with the production of the aromatic ketone by the Friedel-Crafts acylation of an aromatic compound, e.g., isobutylbenzene with an acyl fluoride, a carboxylic acid anhydride, a free carboxylic acid, or a mixture of the foregoing reactants, using an excess of HF as catalyst, to produce the mixture comprising aromatic ketone and HF to be separated, and to which the separated HF and in some cases the acyl fluoride may be recycled.

20 Claims, 1 Drawing Sheet

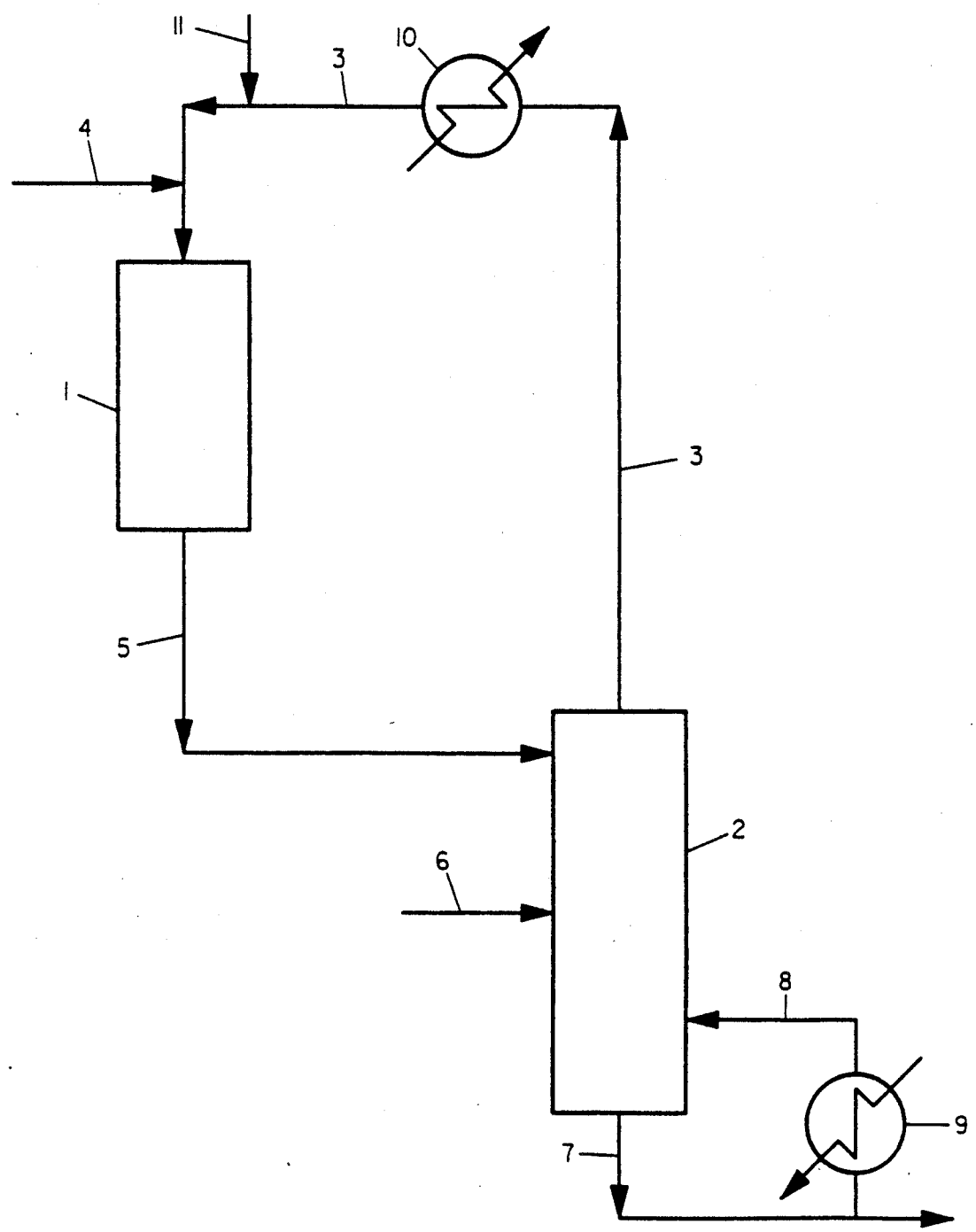

METHOD FOR REMOVING HYDROGEN FLUORIDE FROM MIXTURES COMPRISING AROMATIC KETONES

BACKGROUND OF THE INVENTION

1. Field of the Invention

This invention relates to a method for removing hydrogen fluoride (HF) from mixtures comprising HF and aromatic ketones. More specifically, the invention relates to the removal of hydrogen fluoride from mixtures comprising HF and aromatic ketones resulting from the Friedel-Crafts acylation of an aromatic compound with an acyl fluoride, a carboxylic acid anhydride, a free carboxylic acid or a combination of the foregoing acylating agents, using HF as solvent/catalyst.

2. Description of Related Art

The following information is disclosed in accordance with the terms of 37 CFR 1.56, 1.97, and 1.98.

Aromatic ketones which can be produced by Friedel-Crafts acylations using hydrogen fluoride as solvent/catalyst are possible intermediates for a variety of products having a multiplicity of end uses. Thus, U.S. Pat. No. 4,524,217, issued June 18, 1985 to Davenport et al., discloses a process of using hydroxy aromatic ketones, e.g., 4-hydroxyacetophenone (4-HAP), to make N-acyl-hydroxy aromatic amines, e.g., N-acetyl-para-aminophenol (APAP), better known as acetaminophen, which has wide use as an analgesic. U.S. Pat. No. 4,568,763, issued Feb.4, 1986 to Davenport et al., discloses the use of hydroxy aromatic ketones such as 4-HAP as an intermediate for the production of N-acyl-acyloxy aromatic amines, e.g., 4-acetoxyacetanilide (4-AAA), which can be used for the preparation of poly(ester-amide)s capable of forming an anisotropic melt phase and suitable for being formed into shaped articles such as moldings, fibers, and films. In addition, 4-AAA may also be hydrolyzed to form APAP. U.S. Pat. No. 4,692,546, issued Sept. 8, 1987 to Davenport, discloses a process wherein hydroxy aromatic ketones, e.g., 4-HAP, are used to produce acyloxy aromatic carboxylic acids, e.g., 4-acetoxybenzoic acid (4-ABA), which is also capable of being used directly to make polymers which can be formed into an anistropic melt suitable for the formation of shaped articles. Moreover, 4-ABA can be hydrolyzed to 4-hydroxybenzoic acid (4-HBA) which can be used as an intermediate for the production of preservatives, dyes, and fungicides.

The foregoing U.S. patents and pending applications each shows the production of aromatic ketones by the Friedel-Crafts acylation of aromatic compounds with an acylating agent such as an acyl halide, a carboxylic acid anhydride or a free carboxylic acid, using hydrogen fluoride as solvent/catalyst. In addition to these disclosures, U.S. Pat. No. 4,607,125 issued Aug. 19, 1986 to Mott and pending application Ser. No. 714,407, filed Mar. 21, 1985 by Davenport et al., teach processes for the production of 4-HAP by the Friedel-Crafts acetylation of phenol with acetic anhydride utilizing hydrogen fluoride as catalyst and reaction conditions within certain prescribed ranges.

U.S. Pat. No. 4,593,125, issued June 3, 1986 to Davenport et al., shows the acylation of various substituted naphthalenes using an acylating agent such as an acyl fluoride, a carboxylic acid anhydride or a free carboxylic acid and hydrogen fluoride as catalyst to obtain the corresponding substituted naphthones, e.g., 6-hydroxy-2-acetonaphthone (6, 2-HAN).

Japanese Early-Disclosure (Kokai) 85-188343 published Sept. 25, 1985 discloses the preparation of aromatic ketones by reacting an aromatic compound with an acyl fluoride in the presence of hydrogen fluoride, with the acyl fluoride being separately prepared by reacting an acid anhydride with hydrogen fluoride.

U.S. Pat. No. 4,059,633 issued Nov. 22, 1977 to Childs, discloses a process for the recovery of hexafluoroacetone from a hexafluoroacetone-HF complex with acetic anhydride under reaction conditions. The reaction produces liberated hexafluoroacetone and by-products, acetyl fluoride and acetic acid.

Pending application Ser. No. 158,141 filed Mar. 4, 1988 by Elango et al., shows the production of 4-isobutylacetophenone (4-IBAP) by the Friedel-Crafts acetylation of isobutylbenzene (IBB) with an acetylating agent which may be acetyl fluoride (AcF) acetic anhydride ($Ac_2O$), using a catalyst which may be hydrogen fluoride. The 4-isobutylacetophenone is disclosed as an intermediate in a process for the production of ibuprofen.

In general, processes for producing aromatic ketones by acylating an aromatic compound with an acyl fluoride, a carboxylic acid anhydride, and/or a free carboxylic acid as acylating agent, utilizing hydrogen fluoride as a catalyst, employ an excess of hydrogen fluoride and acylating agent and result in a product mixture comprising hydrogen fluoride and carboxylic acid if anhydride was used as acylating agent as well as aromatic ketone product. Such mixture must be purified both to obtain aromatic ketone of sufficient purity to make it suitable for further use, and to recover the hydrogen fluoride for recycling to the process. Some of the free, i.e., uncomplexed HF may be removed by straight distillation under relatively mild conditions. However, because of the frequent formation of a stable and relatively high boiling complex of aromatic ketone and HF, and a complex of carboxylic acid and HF if carboxylic acid is present in the mixture, removal of sufficient HF necessary to obtain an aromatic ketone of suitable purity may require distillation under vacuum at temperatures so high as to cause an unfavorable loss of aromatic ketone due to polymerization or other side reactions. Thus, any process which achieves a satisfactory level of separation of HF from the aromatic ketone product and from the carboxylic acid, if present, without undue loss of product, is very desirable.

One method of purification includes an initial solvent-assisted distillation (SAD) of the mixture as disclosed, for example, in U.S. Pat. No. 4,663,485, issued May 5, 1987 to Murphy et al., and pending application Ser. No. 013,311 filed Feb. 11, 1987 by Murphy et al. In this method, a composition comprising an aromatic ketone, e.g., 4-hydroxyacetophenone (4-HAP), and an inorganic fluoride consisting essentially of hydrogen fluoride (HF), is distilled in a column or other vessel in the presence of an assisting solvent which is stable in the presence of HF. The vapor overhead comprises a major portion of the HF in the feed to the distillation vessel mixed with some assisting solvent. A liquid residue containing solvent and most of the aromatic ketone in the feed and which may contain heavy ends other than the desired aromatic ketone, is obtained from the base of the column. When the composition being purified is that resulting from the acylation of an aromatic compound with an acyl fluoride and/or a carboxylic acid anhydride using HF as a solvent/catalyst, and thus contains aromatic ketone, HF, and some carboxylic acid if the anhydride was used as all or part of the acylating agent, then the overhead in the solvent-assisted distillation column will contain HF, assisting solvent, and carboxylic acid if present. After separation of the assisting solvent by decantation or distillation (assuming the assisting solvent is not the carboxylic acid) the composition remaining will comprise HF, and carboxylic acid if present, with possibly a small amount of assisting solvent. However, before recycling HF to the process (a step necessary for economic reasons), the carboxylic acid must be separated or substantially reduced in content since its presence inhibits the acylation reaction due to equilibrium considerations.

While the foregoing solvent-assisted distillation alone is generally effective in reducing the level of HF in the aromatic ketone to a lower level than could be obtained by straight distillation of the mixture at a temperature which does not cause substantial decomposition of the ketone, such an HF level is often still too high for many applications of the aromatic ketone. Furthermore, solvent-assisted distillation, when used as the sole method for reducing the HF in an aromatic ketone to a prescribed level, may have other disadvantages, such as mutual solubility, high cost of equipment, excessive foam formation, and contamination and high energy cost due to the use of large amounts of assisting solvent.

SUMMARY OF THE INVENTION

In accordance with one aspect of this invention, hydrogen fluoride is separated from mixtures comprising an aromatic ketone in which the keto carbon atom is directly bonded to an aromatic ring carbon atom by adding a carboxylic acid anhydride to the mixture while maintaining such mixture at conditions sufficient to sustain a reaction between the anhydride and the hydrogen fluoride to form the corresponding acyl fluoride and carboxylic acid. The acyl fluoride reaction product is generally more volatile than the carboxylic acid or the aromatic ketone and can be easily stripped from the mixture.

In accordance with another aspect of the invention, the foregoing separation of hydrogen fluoride from a mixture also containing an aromatic ketone is integrated in an overall process with the synthesis of the aromatic ketone by the Friedel-Crafts acylation of an aromatic compound with an acyl fluoride, a carboxylic acid anhydride, a free carboxylic acid or a mixture of the foregoing reactants as acylating agent, together with an excess of hydrogen fluoride as solvent/catalyst. If a free carboxylic acid is used as all or part of the acylating agent, some of its anhydride is generally also added to react with the water of reaction. The resulting product mixture comprising an aromatic ketone complexed with HF, a possible excess of carboxylic acid complexed with HF (especially if anhydride was used as all or part of the acylating agent), and uncomplexed HF is then subjected to a stripping operation under conditions mild enough to separate that part of the HF which is not complexed with the aromatic ketone and carboxylic acid, if present, without subjecting the ketone to excessive decomposition. The separated HF together with light components in some instances, e.g. the acyl fluoride and unreacted aromatic hydrocarbon, are recycled to the acylation reaction and a carboxylic acid anhydride is added to the remaining composition to form acyl fluoride and carboxylic acid as previously described.

DESCRIPTION OF THE DRAWING

The drawing is a schematic diagram of an integrated process illustrating the invention.

DESCRIPTION OF PREFERRED EMBODIMENTS

The aromatic ketones contemplated to be purified by the process of this invention have the formula

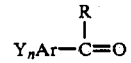

where Ar is the residue of an unsubstituted aromatic hydrocarbon, preferably benzene, naphthalene or biphenyl, wherein hydrogen atoms are substituted with the keto carbon atom and Y's indicated in the formula, n is an integer in the range of zero to about 5, preferably 1 to 3, and the Y's may be any substituent which is stable in the presence of HF and does not cause the ketone to decompose on melting, such as hydroxy, sulfhydryl, halide, e.g. fluoride, chloride, bromide, or iodide and/or organic, e.g., alkyl, alkoxy, acyloxy, or alkylthio, containing from 1 to about 18 carbon atoms, preferably 1 to 4 carbon atoms. In cases where there are at least two Y's bonded to the aromatic nucleus, they may be the same or different.

The R group in the foregoing formula is an alkyl group containing, for example 1 to 18 carbon atoms, preferably 1 to 4 carbon atoms, or aryl, e.g. phenyl or naphthyl. More preferably, R is methyl, ethyl, propyl, or phenyl and most preferably methyl, such that the aromatic ketone being purified is an aromatic methyl ketone.

A group of aromatic ketones particularly suited to being purified by the process of this invention are alkyl, alkoxy or hydroxy aromatic ketones such that, in the foregoing formula, Y is alkyl or alkoxy containing 1 to 4 carbon atoms, or hydroxy, n is 1, R is methyl, and Ar is 1, 4-phenylene, 2, 6-naphthylene, 2, 1-naphthylene, 5-phenyl-1, 2-phenylene, 3-phenyl-1, 4-phenylene, or 3-methyl-1, 4-phenylene, with the ketocarbon occupying the first stated numbered position of Ar when the positions are not equivalent. Most preferably Ar is 1, 4-phenylene or 2, 6-naphthalene, and the aromatic ketone being purified is 4-isobutylacetophenone (4-IBAP), 4-hydroxyacetophenone (4-HAP), 6-hydroxy-2-acetonaphthone (6, 2-HAN), 6-methoxy-2-acetonaphthone, or 4-methylacetophenone (4-MAP).

Another group of aromatic ketones suitable for purification by the process of this invention are the benzophenones, wherein Ar in the foregoing formula is a benzene residue and R is phenyl, e.g., benzophenone and 2, 3, 4-trihydroxybenzophenone.

The compositions containing an aromatic ketone and HF which are treated to separate these components utilizing the process of this invention are obtained, for example, as effluents from the production of aromatic ketones, e.g., 4-IBAP, by the Friedel-Crafts acylation of an aromatic compound, e.g., isobutylbenzene, using HF as solvent/catalyst as taught, for example in the previously cited disclosures. In most cases, such compositions contain a molar preponderance of liquid HF in which is dissolved a product of reaction composed primarily of the desired aromatic ketone together with minor amounts of impurities such as isomeric aromatic ketones, e.g., 3-isobutylacetophenone (3-IBAP), when 4-IBAP is the desired product, and initial reactants, e.g., isobutylbenzene. Depending on the nature of the process used to produce it, the amount of aromatic ketone in the composition, excluding the HF, may be, for example in the range of about 25 to 98 weight percent, while the mole ratio of HF to aromatic ketone plus impurities may be, for example about the same as the mole ratio of HF to initial aromatic reactant, e.g., isobutylbenzene, in the Friedel-Crafts acylation of such aromatic compound, in cases where the latter reaction is used to prepare the aromatic ketone, e.g., 4-IBAP. As more fully discussed below, this mole ratio may be, for example, about 7 to 80.

It is preferable that HF is the only inorganic fluoride present in significant quantity, i.e., there is no other inorganic fluoride present, e.g., $BF_3$, in such quantity as would materially change the basic and novel characteristics of the process. Expressed another way, the inorganic fluoride present in any of the compositions involved in the method of the invention preferably "consists essentially" of hydrogen fluoride.

The reaction of carboxylic acid anhydride with the HF in the composition comprising an aromatic ketone intended to be treated to remove HF in accordance with this invention is indicated by the following equation:

(R'CO)$_2$O+HF→R'COF+R'COOH

In the formulas of this equation, R' is any suitable organic radical, e.g. alkyl or aryl such as phenyl but is preferably an alkyl group of 1 to 3 carbon atoms so that the anhydride is, for example, acetic anhydride, propionic anhydride or isobutyric anhydride, resulting in the formation of the corresponding fluorides and free carboxylic acids.

As stated, the mixture comprising aromatic ketone and HF is preferably heated before coming in contact with anhydride at a temperature below that at which the aromatic ketone tends to decompose in the presence of HF, e.g., a temperature of about 30° to 155° C., at a pressure of about 0 to 25 psig, so as to separate most of the excess HF, i.e., that which is above the amount necessary to complex with the aromatic ketone and carboxylic acid present. After the initial HF separation, the mixture is contacted with a carboxylic acid anhydride which reacts with the HF to produce the corresponding acyl fluoride and free carboxylic acid. The acyl fluoride can be easily stripped from the ketone because of its much lower boiling point, while the free carboxylic acid can usually be readily separated from the ketone in a subsequent distillation operation.

The foregoing process can be readily carried out as consecutive batch operations. Preferably, however, it is carried out continuously or semi-continuously in a distillation or stripping column wherein the initial mixture comprising aromatic ketone and HF is added closer to the top of the column and anhydride is added at one or more points lower down in the column. Heat is added to the column to maintain temperatures such that the excess, uncomplexed HF is stripped from the mixture in that part of the column above where the anhydride is added, so that it doesn't contact the anhydride, the reaction between anhydride and HF below where the anhydride is added proceeds at a satisfactory rate, and the resulting acyl fluoride is also stripped from the ketone substantially completely and leaves the column with the stripped HF. In the case of the reaction between acetic anhydride and HF to produce acetyl fluoride and acetic acid (whether batch or continuous), the reaction and stripping operations may be carried out at temperatures, for example, in the range of about 30° to 155° C. and pressures in the range, for example, of about 0 to 25 psig.

The inventive method of removing HF from a mixture comprising an aromatic ketone by reacting the HF with an anhydride, is preferably combined as an integrated process with the anhydrous production of the aromatic ketone by the Friedel-Crafts acylation of an aromatic compound with an acyl fluoride, a carboxylic acid anhydride, and/or a free carboxylic acid using HF as solvent/catalyst, as shown in the following equation:

$$Y_nArH + X-\underset{\underset{R}{|}}{C}=O \xrightarrow{HF} Y_nAr\underset{\underset{R}{|}}{C}=O + HX$$

where Ar, R and Y have the meanings previously given, and X is F·

$$[O=\underset{\underset{R}{|}}{C}-O-], \text{ or } -OH.$$

As previously stated, if free carboxylic acid is used as all or part of the acylating agent, some of its anhydride is usually added to further react with the water of reaction. The product of the reaction thus comprises the aromatic ketone and HF and/or free carboxylic acid, with HF being present in appreciable amount in either case because of the large excess used as solvent/catalyst. This product stream is then treated to remove the HF from the aromatic ketone by initial stripping of uncomplexed HF, reaction of the complexed HF with anhydride to form an acyl fluoride and free carboxylic acid, and stripping of the acyl fluoride from the aromatic ketone. The stripped HF is then recycled to the reaction as solvent/catalyst with other light components in some instances, as previously described.

The reaction for producing the aromatic ketone may be, for example, a stirred batch reactor, an extractor-reactor, or a continuous staged reactor. In a stirred batch reactor, the aromatic hydrocarbon, acylating agent and HF are stirred at the desired temperature until the batch reaction is complete and the entire batch is further treated in accordance with the process of this invention. In an extractor-reactor, the aromatic hydrocarbon such as isobutylbenzene, which is insoluble in HF and is the discontinuous phase in a continuous phase comprising HF, reacts with the acylating agent, e.g. acetyl fluoride, to form the aromatic ketone, e.g., 4-isobutylacetophenone (4-IBAP). The ketone is extracted into the HF phase and leaves the reactor with that phase which is further processed in accordance with the invention. The unreacted aromatic hydrocarbon phase rises through the HF phase and is withdrawn from the top of the reactor and recycled to the bottom where it is again subjected to reaction with the acetylating agent. In a staged continuous reactor, the aromatic hydrocarbon is continuously fed concurrent with the HF and is reacted with acylating agent to form aromatic ketone in one pass. The product comprising the aromatic ketone, HF, and any aromatic hydrocarbon remaining unreacted is continuously withdrawn from the reactor and further treated in accordance with the process of the invention.

It is preferred for the foregoing integrated process that acyl groups of the aromatic ketone and the anhydride used to remove HF from the ketone be the same, so that the acyl fluoride formed by the reaction of anhydride with the HF can be recycled with the stripped HF to the reaction as acylating agent. Most preferably such acyl groups are acetyl as in the production of an aromatic methyl ketone by reacting an aromatic compound with acetyl fluoride and optionally acetic anhydride, and treating the ketone containing product with acetic anhydride to remove HF and produce acetyl fluoride which can then be recycled to the reaction as acylating agent with the stripped excess HF.

As a further example of the inventive method, it is possible to remove the HF from a mixture comprising an aromatic ketone by contacting the mixture with a carboxylic acid anhydride in which the acyl groups are different from those of the acyl fluoride, carboxylic acid, and/or carboxylic anhydride utilized as acylating agent in the Friedel-Crafts acylation of an aromatic compound in the presence of HF as catalyst to produce the aromatic ketone. Thus, in the production of benzophenone or a substituted benzophenone by the Friedel-Crafts acylation of benzene or a substituted benzene with benzoyl fluoride utilizing HF as catalyst, the product of reaction comprising the benzophenone and HF, after stripping the free uncomplexed HF from the mixture, may be treated with acetic anhydride, which reacts with HF to produce acetyl fluoride and acetic acid. The acetyl fluoride can be separated from the mixture but, instead of being recycled to the reactor (since a benzophenone rather than an acetophenone is being produced), the acetyl fluoride may be reacted with benzoic acid to produce benzoyl fluoride and acetic acid. These compounds can then be easily separated by distillation, with the HF and benzoyl fluoride being recycled to the Friedel-Crafts reaction.

The process of this invention may be utilized in conjunction with the operation of a solvent-assisted distillation (SAD) column for the separation of aromatic ketone from HF as disclosed in previously cited U.S. Pat. No. 4,663,485 and pending application Ser. No. 013,311, the entire disclosures of which are incorporated by reference. Thus, the amount of HF still mixed with the aromatic ketone taken from the bottom of the SAD column may be further reduced, and/or the energy requirements and amount of circulating assisting solvent may be reduced, by adding a carboxylic acid anhydride to the SAD column at a point below the introduction of the feed and at which the free uncomplexed HF has been substantially completely separated by vaporization. The anhydride will react with HF complexed with aromatic ketone and any carboxylic acid which may be present in the column, thus reducing the amount of HF which would otherwise be withdrawn from the bottom of the column with the aromatic ketone. Depending on its volatility and whether it is being used as an acylating agent in the reactor, the resulting acyl fluoride may be recycled to the reactor as an uncondensed vapor or as a liquid mixed with HF condensed from the SAD column overhead. If the acyl fluoride resulting from the anhydride-HF reaction is not the acylating agent for the reaction, e.g., is acetyl fluoride whereas the acylating agent is benzoyl fluoride as previously described, then such acyl fluoride may be separately condensed or separated from the other overhead components by distillation and reacted with the appropriate carboxylic acid, e.g., benzoic acid, to obtain the acyl fluoride which is being used as the reaction acylating agent, e.g., benzoyl fluoride.

Alternative to injection of the anhydride into the SAD column as described, the aromatic ketone taken from the bottom of the SAD column which still contains some HF may be treated with anhydride as described to completely remove or substantially reduce the amount of such HF.

As stated, the separation of HF from an aromatic ketone by reacting the HF with a carboxylic acid anhydride may be carried out in a distillation vessel. Any suitable distillation vessel may be used for this purpose. Thus, the vessel may or may not contain interior surfaces serving to implement condensation and re-vaporization of the constituents of the reacting composition, e.g., packing, trays, and the like. For continuous or semi-continuous operation, the use of a fractionating column, e.g., a packed column or a column containing trays, is particularly suitable. When operating continuously, the mixture comprising aromatic ketone and HF, and the anhydride may be premixed before entering the column. Preferably, however, they are injected into the column at separate points, as previously described.

The drawing is a schematic representation of an integrated process for preparing an aromatic ketone by the Friedel-Crafts acylation of an aromatic compound with an acyl fluoride using HF as catalyst to form a ketone/HF complex, and removing HF from the complex by reacting it in a stripping column with a carboxylic acid anhydride.

Into reactor 1 is fed a mixture of a relatively volatile acyl fluoride, e.g., acetyl fluoride, and HF which has been recycled from stripping column 2 through line 3, and to which has been added an aromatic compound, e.g., 4-isobutylbenzene or phenol, through line 4. Alternatively, a free carboxylic acid, e.g., acetic acid, may also be fed to line 3 through line 11, with the mixture of acyl fluoride and free carboxylic acid behaving similarly to a carboxylic acid anhydride, e.g., acetic anhydride feed to the reactor. Conditions in reactor 1 are maintained such that the aromatic ketone is subjected to a Friedel-Crafts acylation with the acyl fluoride in the presence of HF as catalyst to form an aromatic ketone, e.g., 4-isobutylacetophenone (4-IBAP) or 4-hydroxyacetophenone (4-HAP), complexed with HF which is also a product of reaction. The product composition comprising the ketone/HF complex, free, uncomplexed HF, unreacted aromatic compound, unreacted acyl fluoride, and, if an excess of free carboxylic acid, e.g., acetic acid, was added, a carboxylic acid/HF complex, is fed through line 5 to the top of stripping column 2 which is equipped with trays for the fractional distillation of the components of the feed composition as conventional in the art. At some point below line 5 at which the product composition is fed to column 2, a carboxylic acid anhydride is injected into the column through line 6 for the purpose of reacting with the HF in the ketone/HF complex, and, if present, the carboxylic acid/HF complex, contained in the feed composition to form a relatively volatile acyl fluoride, e.g., acetyl fluoride, and a carboxylic acid, e.g., acetic acid. The free uncomplexed HF is stripped from the feed composition in that part of the column between feed composition line 5 and anhydride line 6. Below line 6, the relatively volatile acyl fluoride which forms as a result of the reaction between the anhydride and the HF in the ketone/HF complex and, if present, the carboxylic acid/HF complex, is stripped from the liquid comprising the ketone, carboxylic acid and, depending on its volatility, unreacted aromatic compound. The latter liquid leaves the bottom of column 2 through line 7 with part of it being recycled to column 2 through line 8 after being vaporized in reboiler 9 and the remainder being withdrawn from the system for further processing. At the top of column 2, HF, acyl fluoride and, again depending on its volatility, unreacted aromatic compound are withdrawn through line 3 as vapor and, after being condensed in heat exchanger 10, are recycled together with free carboxylic acid, if added through line 11, as liquid to the top of reactor 1. A portion of the condensate may also be returned as reflux to column 2.

As an alternative to the foregoing process, all or part of the acyl fluoride, e.g., acetyl fluoride, leaving column 2 through line 3 may be separated from the HF and recovered, with all or part of the acylation requirement in reactor 1 being supplied by carboxylic acid anhydride, e.g., acetic anhydride, or by a mixture of the free carboxylic acid and acyl fluoride, or the acyl fluoride leaving column 2 may be reacted with a carboxylic acid containing a different acyl group, e.g., benzoic acid, to form a different acyl fluoride, e.g., benzoyl fluoride, which may be sent to reactor 1 as primary acylating agent.

The following examples further illustrate the invention.

EXAMPLE 1

To a batch, stirred tank reactor were added 50 moles of HF, 2 moles of acetic anhydride, and 1 mole of isobutylbenzene, and the composition was reacted at 80° C. for 3 hours. The resulting product mixture contained a 4-IBAP/HF complex, an acetic acid/HF complex, free uncomplexed HF, and some unreacted isobutylbenzene.

A 16-tray distillation column with a forced circulation reboiler was prepared for operation by first charging it with acetic acid, setting the pressure control at 5 psig, and introducing steam to the reboiler. When the temperature at tray 13 reached 100° C., feed of 2.15 g/min. of acetic anhydride was begun at tray 7 of the column. Shortly thereafter feed of the described product mixture at tray 16 was begun at the rate of 10 g/min. When steady state conditions were reached, the tray temperature control keeping the temperature at tray 13 at 100° C. was switched to automatic. After 2 hours of operation, the 4-IBAP containing liquid in tray 1, i.e., the tray just above the reboiler, was found to contain only 60 ppm of fluoride. Such fluoride is the total of that found in HF and the acetyl fluoride formed as a result of the reaction between HF and acetic anhydride. Most of the free uncomplexed HF was separated as vapor between tray 16 and tray 7 and was withdrawn from the top of the column with vaporized acetyl fluoride. The HF is suitable for being reused in the reaction as catalyst and the acetyl fluoride may be reacted with acetic acid to form additional acetic anhydride which may be reused in reactor 1 as acylating agent or in column 2 to react with additional HF complexes.

EXAMPLE 2

The procedure of Example 1 was followed except that the feed rate of acetic anhydride at tray 16 was 3.25 g/min. After 5 hours of operation, the 4-IBAP containing liquid sampled from tray 1 was found to contain 108 ppm of fluoride, while the liquid at the base, i.e., from the reboiler, was found to contain 10 ppm of fluoride.

EXAMPLE 3

The procedure of Example 1 was followed except the temperature at tray 13 was controlled at 80° C. After 3 hours of operation, the liquid on tray 1 contained 286 ppm of fluoride.

EXAMPLE 4

The procedure of Example 1 was followed except that the temperature at tray 13 was controlled at 60° C. After 3 hours of operation, the liquid on tray 1 contained 1.24 wt. % of fluoride.

The results of the foregoing examples illustrate the effectiveness of the inventive method in reducing the amount of HF complexed with an aromatic ketone, e.g., 4-IBAP. The following comparative example illustrates the results obtained when the product composition is subjected to an identical stripping operation except that the inventive method is not employed, i.e., no acetic anhydride is passed into the column.

COMPARATIVE EXAMPLE

The procedure of Examples 1 and 2 was followed except that no acetic anhydride was passed into the column. After 3 hours of operation, the liquid on tray 1 contained 2.4 wt. % of fluoride and the base liquid contained 1.2 wt. % of fluoride. The results of this example thus show that stripping alone results in an aromatic ketone product containing a much larger fluoride content than if stripping is combined with anhydride addition.

EXAMPLE 5

This example illustrates an integrated continuous process for the production of an aromatic ketone by acylation of an aromatic hydrocarbon in the presence of HF as solvent/catalyst and the removal of HF from the complex formed with the ketone, as shown in the drawing.

Isobutylbenzene (IBB) (10.2 lb/hr) and a solution of HF containing 13 wt % HOAc and 12 wt % acetyl fluoride (AcF) (153 lb/hr) were fed into reactor 1 through line 4. The mixture was reacted at 60° C. for 1.5 hrs to produce the desired 4-isobutylacetophenone product.

The HF solution containing the product was fed through line 5 to tray 28 of a 30 tray stripping column 2 operated at 8-25 psig. Acetic acid in the base of the column was vaporized in reboiler 9, and when the feed solution was contacted with the hot vapor, the light components were stripped overhead. The majority of the HF in the feed solution was stripped overhead along with AcF, while the HF complexed to the product isobutylacetophenone was carried with the solvent acetic acid to the lower section of the column. The heat duty to the reboiler was controlled by maintaining tray 22 of the column at 90°-100° C. such that essentially no HOAc was distilled overhead. The overhead stream in line 3 was mixed with 20 lb/hr HOAc from line 11 before being recycled back to reactor 1. Acetic anhydride was fed through line 6 at 7 lb/hr to tray 5 of column 2 to liberate the product from the remaining HF and produce AcF overhead in the column.

Acetic acid solution continuously recovered from the base of the distillation column contained 35 wt % 4-IBAP, 0.4 wt % IBB, 2.4% Ac$_2$O, and 4% aromatic by-products. The solution was found to contain only 44 ppm fluoride.

We claim:

1. A method of separating hydrogen fluoride (HF) from a mixture comprising HF complexed with an aromatic ketone in which the keto carbon atom is directly bonded to an aromatic ring carbon atom, by adding a carboxylic acid anhydride to the mixture while maintaining the mixture a conditions sufficient to sustain a reaction between the anhydride and the HF to form the corresponding acyl fluoride and carboxylic acid, and separating said acyl fluoride from said mixture.

2. The method of claim 1 wherein said anhydride has the formula (R'CO)₂O with R' being an alkyl group of 1 to 3 carbon atoms.

3. The method of claim 2 wherein said anhydride is acetic anhydride and said acyl fluoride is acetyl fluoride.

4. The method of claim 3 wherein said aromatic ketone is 4-isobutylacetophenone, 4-hydroxyacetophenone, 6-hydroxy-2-acetonaphthone, 6-methoxy-2-acetonaphthone, or 4-methylacetophenone.

5. The method of claim 4 wherein said aromatic ketone is 4-isobutylacetophenone.

6. The method of claim 4 wherein said aromatic ketone is 4-hydroxyacetophenone.

7. The method of claim 1 wherein said mixture contains uncomplexed HF in addition to said HF complexed with an aromatic ketone, said mixture is fed near the top of a stripping column, said anhydride is fed to said stripping column at one or more points below said mixture, and said stripping column is operated under conditions such that said uncomplexed HF is substantially stripped from said mixture between the feed points of said mixture and anhydride, said anhydride reacts with the complexed HF below the feed point or points of said anhydride to form said acyl fluoride and carboxylic acid, said acyl fluoride is stripped from the mixture and is withdrawn with said stripped HF from the top of the column, and said aromatic ketone is withdrawn from the bottom of said column.

8. The method of claim 7 wherein said anhydride is acetic anhydride and said acyl fluoride is acetyl fluoride.

9. The method of claim 8 wherein said aromatic ketone is 4-isobutylacetophenone.

10. The method of claim 8 wherein said aromatic ketone is 4-hydroxyacetophenone.

11. A method of producing an aromatic ketone in which the keto carbon atom is directly bonded to an aromatic ring carbon atom comprising subjecting an aromatic compound to a Friedel-Crafts acylation with an acyl fluoride, a carboxylic acid anhydride, a free carboxylic acid or a mixture of the foregoing reactants as acylating agent, and an excess of hydrogen fluoride (HF) as solvent/catalyst, to obtain a product mixture comprising an aromatic ketone complexed with HF, a carboxylic acid complexed with HF if said anhydride was used as all or part of the acylating agent, and uncomplexed HF, feeding said product mixture to a point near the top of a stripping column, feeding to said stripping column at one or more points below the feed point of said product mixture a carboxylic acid anhydride of the formula (R'CO)₂O wherein R' is an alkyl group of 1 to 3 carbon atoms, substantially stripping said uncomplexed HF between the feed points of said product mixture and said latter anhydride, reacting said latter anhydride with the complexed HF below the feed point of said anhydride to form an acyl fluoride and a carboxylic acid, stripping said acyl fluoride from the mixture, withdrawing said HF and acyl fluoride from the top of the column, recycling the HF to said Friedel-Crafts acylation, and withdrawing said aromatic ketone from the bottom of the column.

12. The method of claim 11 wherein said acylating agent is an acyl fluoride which is the same as that formed in said stripping column by reaction of HF and carboxylic acid anhydride, with the latter acyl fluoride being recycled with HF from the stripping column to said Friedel-Crafts acylation.

13. The method of claim 12 wherein said anhydride fed to the stripping column is acetic anhydride and said acyl fluoride is acetyl fluoride.

14. The method of claim 1 wherein said aromatic ketone is 4-isobutylacetophenone, and said aromatic compound is isobutylbenzene.

15. The method of claim 13 wherein said aromatic ketone is 4-hydroxyacetophenone and said aromatic compound is phenol.

16. The method of claim 11 wherein said aromatic ketone is a benzophenone, said acylating agent is benzoyl fluoride, said anhydride fed to the stripping column is acetic anhydride, and said acyl fluoride formed in said stripping column is acetyl fluoride which, after being withdrawn from said column, is reacted with benzoic acid to form benzoyl fluoride which is recycled to said Friedel-Crafts acylation.

17. The method of claim 1 wherein said aromatic ketone has the formula $$Y_nAr-\overset{R}{\underset{|}{C}}=O$$

where Ar is the residue of benzene, naphthalene or biphenyl, whose hydrogen atoms are substituted with the keto carbon atom and Y's indicated in the formula, n is an integer in the range of zero to 5, the Y's are the same or different and are each sulfhydryl, halide, alkyl, alkoxy, acyloxy, or alkylthio, the latter four substituents containing from 1 to 18 carbon atoms, and R is an alkyl group containing 1 to 18 carbon atoms, phenyl or naphtyl.

18. The method of claim 17 wherein R is methyl, ethyl, propyl, or phenyl.

19. The method of claim 18 wherein Y is hydroxy, or alkyl or alkoxy containing 1 to 4 carbon atoms, n is 1, R is methyl, and Ar is 1, 4- phenylene, 2, 6- naphthylene, 2, 1- naphthylene, 5- phenyl-1, 2- phenylene, 3- phenyl-1, 4- phenylene, or 3- methyl-1, 4- phenylene, with the ketocarbon occupying the first stated numbered position of Ar when the positions are not equivalent.

20. The method of claim 8 wherein said reaction and stripping operations are carried at temperatures in the range of about 30° to 155° C. and pressures in the range of about 0 to 25 psig.

* * * * *

UNITED STATES PATENT AND TRADEMARK OFFICE
CERTIFICATE OF CORRECTION

PATENT NO. : 4,990,681
DATED : February 5, 1991
INVENTOR(S) : Thomas A. Curtis et al.

It is certified that error appears in the above—identified patent and that said Letters Patent is hereby corrected as shown below:

On the title page, the following Assignee should be present:

[73] Assignee: Hoechst Celanese Corporation
Somerville, New Jersey

Signed and Sealed this

Eighth Day of December, 1992

Attest:

DOUGLAS B. COMER

*Attesting Officer*  *Acting Commissioner of Patents and Trademarks*